US010729762B2

(12) United States Patent
Amara et al.

(10) Patent No.: US 10,729,762 B2
(45) Date of Patent: Aug. 4, 2020

(54) HIV IMMUNE STIMULATING COMPOSITIONS COMPRISING RECOMBINANTLY EXPRESSED PILI ON BACTERIA AND METHODS RELATED THERETO

(71) Applicant: Emory University, Atlanta, GA (US)

(72) Inventors: Rama Rao Amara, Decatur, GA (US); June Scott, Atlanta, GA (US); Bernard Quigley, Atlanta, GA (US); Venkateswarlu Chamcha, Atlanta, GA (US)

(73) Assignee: Emory University, Atlanta, GA (US)

( * ) Notice: Subject to any disclaimer, the term of this patent is extended or adjusted under 35 U.S.C. 154(b) by 161 days.

(21) Appl. No.: 15/848,706

(22) Filed: Dec. 20, 2017

(65) Prior Publication Data

US 2018/0125967 A1  May 10, 2018

Related U.S. Application Data

(62) Division of application No. 14/422,490, filed as application No. PCT/US2013/058383 on Sep. 6, 2013, now Pat. No. 9,861,693.

(Continued)

(51) Int. Cl.
*A61K 39/21* (2006.01)
*C07K 14/005* (2006.01)
(Continued)

(52) U.S. Cl.
CPC .............. *A61K 39/21* (2013.01); *A61K 39/12* (2013.01); *A61K 45/06* (2013.01); *C07K 14/005* (2013.01);
(Continued)

(58) Field of Classification Search
None
See application file for complete search history.

(56) References Cited

U.S. PATENT DOCUMENTS 6,913,750 B2    7/2005   Hultgren
9,861,693 B2    1/2018   Amara
(Continued)

FOREIGN PATENT DOCUMENTS

WO    1997009437    3/1997
WO    2009027768    3/2009
WO    2009137763    11/2009

OTHER PUBLICATIONS

Xin et al. "Immunogenicity and protective efficacy of orally administered recombinant Lactococcus lactis expressing surface-bound HIV Env", Blood, 2003; 102(1):223-228.*

(Continued)

*Primary Examiner* — Janet L Andres
*Assistant Examiner* — Stuart W Snyder
(74) *Attorney, Agent, or Firm* — Emory Patent Group

(57) ABSTRACT

This disclosure relates to recombinant bacteria, e.g. *L. lactis*, expressing heterologous pili containing human immunodeficiency virus (HIV) antigens. In certain embodiments, the recombinant bacteria are administered in combination with other HIV antigens, nucleic acids encoding HIV antigens, recombinant virus encoding HIV antigens, anti-viral agents and/or adjuvants in an effective amount to elicit a mucosal immune response against HIV.

4 Claims, 6 Drawing Sheets

Specification includes a Sequence Listing.

Related U.S. Application Data

(60) Provisional application No. 61/698,200, filed on Sep. 7, 2012.

(51) Int. Cl.
| | | |
|---|---|---|
| *A61K 39/12* | (2006.01) | |
| *A61K 45/06* | (2006.01) | |
| *C12N 7/00* | (2006.01) | |
| *A61K 39/00* | (2006.01) | |

(52) U.S. Cl.
CPC .......... *C12N 7/00* (2013.01); *A61K 2039/523* (2013.01); *A61K 2039/542* (2013.01); *A61K 2039/545* (2013.01); *A61K 2039/55516* (2013.01); *A61K 2039/55544* (2013.01); *A61K 2039/55561* (2013.01); *A61K 2039/55594* (2013.01); *C12N 2710/24143* (2013.01); *C12N 2740/15022* (2013.01); *C12N 2740/16034* (2013.01); *C12N 2740/16234* (2013.01)

(56) References Cited

U.S. PATENT DOCUMENTS

| | | |
|---|---|---|
| 2008/0026988 A1 | 1/2008 | Baker |
| 2011/0189236 A1 | 8/2011 | Scott |
| 2018/0125967 A1 | 5/2018 | Amara |

OTHER PUBLICATIONS

Quigley et al. "A Foreign Protein Incorporated on the Tip of T3 Pili in Lactococcus lactis Elicits Systemic and Mucosal Immunity", Infect. Immun. 2010; 78(3: 1294-1303).*
Kajikawa et al. ("Construction and Immunological Evaluation of Dual Cell Surface Display of HIV-1 Gag and *Salmonella enterica* Serovar Typhimurium FliC in Lactobacillus acidophilus for Vaccine Delivery", Clin. Vacc. Immunol. 2012; 19(9): 1374-1381.*
Aggarwal et al. Augmentation of HIV-1 Subtype C Vaccine Constructs Induced Immune Response in Mice by CpG Motif 1826-ODN, Viral Immunol. 2005, 18(1):213-23.
Bahey-El-Din et al. "Lactococcus lactis-based vaccines: Current status and future perspectives" Human Vaccines, 7(1): 106-109.
Brenchley et al. "CD4+ T cell depletion during all stages of HIV disease occurs predominantly in the gastrointestinal tract" J Exp Med., 2004; 200(6): 749-759.
Buccato et al. Use of Lactococcus lactis Expressing Pili from Group B *Streptococcus* as a Broad-Coverage Vaccine against Streptococcal Disease, J Infectious Diseases 2006, 194:331-40.
Chamcha et al. Oral immunization with a recombinant Lactococcus lactis expressing HIV-1 Gag on the tip of the pilus induces strong mucosal immune responses, Retrovirology, 2012; 9(Suppl 2): O12.
Chamcha et al. "Oral Immunization with a Recombinant Lactococcus lactis-Expressing HIV-1 Antigen on Group A *Streptococcus* Pilus Induces Strong Mucosal Immunity in the Gut" J Immunol, 2015; 195: 5025-5034.
Chen, Mucosal and Systemic Immune Responses to Chimeric Fimbriae Expressed by *Salmonella enterica* Serovar Typhimurium Vaccine Strains, Infection and Immunity, 2000, p. 3129-3139.
Dramsi et al.,Covalent attachmentof proteins to peptidoglycan, FEMS Microbiol Rev 32 (2008) 307-320.
Goepfert et al. "Phase 1 Safety and Immunogenicity Testing of DNA and Recombinant Modified Vaccinia Ankara Vaccines Expressing HIV-1 Virus-like Particles" The Journal of Infectious Diseases, 2011; 203: 610-619.
Kajikawa et al. "Dissimilar Properties of Two Recombinant Lactobacillus acidophilus Strains Displaying *Salmonella* FliC with Different Anchoring Motifs" Appl. Environ. Microbiol., 2011; 77(18): 6587-6596.
Kajikawa et al. "Construction and immunological evaluation of dual cell surface display of HIV-1 gag and *Salmonella enterica* serovar Typhimurium FliC in Lactobacillus acidophilus for vaccine delivery" Clin Vaccine Immunol., 2012; 19(9): 1374-1381.
Kintu et al. "Feasibility and Safety of ALVAC-HIV vCP1521 Vaccine in HIV-Exposed Infants in Uganda: Results From the First HIV Vaccine Trial in Infants in Africa" Acquir Immune Defic Syndr; 2013; 63(1): 1-8.
Lei et al. "Evaluation of oral immunization with recombinant avian influenza virus HA1 displayed on the Lactococcus lactis surface and combined with the mucosal adjuvant cholera toxin subunit B" Clin Vaccine Immunol., 2011; (7): 1046-1051.
Li et al. "Peak SIV replication in resting memory CD4+ T cells depletes gut lamina propria CD4+ T cells" Nature, 2005; 434(7037): 1148-1152.
MacGregor et al. Plasmid vaccination of stable HIV-positive subjects on antiviral treatment results in enhanced CD8 T-cell immunity and increased control of viral "blips", Vaccine 23 (2005) 2066-2073.
Mandlik et al. Pili in Gram-positive bacteria: assembly, involvement in colonization and biofilm development Trends Microbiol. Jan. 2008 ; 16(1): 33-40.
Mattapallil et al. "Massive infection and loss of memory CD4+ T cells in multiple tissues during acute SIV infection" Nature, 2005; 434(7037): 1093-1097.
Pillai et al. "Different Patterns of Expansion, Contraction and Memory Differentiation of HIV-1 Gag-Specific CD8 T Cells Elicited by Adenovirus Type 5 and Modified Vaccinia Ankara Vaccines" Vaccine, 2011; 29(33): 5399-5406.
Quigley et al., Linkage of T3 and Cpa pilins in the *Streptococcus pyogenes* M3 pilus, Molecular Microbiology (2009) 72(6), 1379-1394.
Quigley et al., A Foreign Protein Incorporated on the Tip of T3 Pili in Lactococcus lactis Elicits Systemic and Mucosal Immunity, Infection and Immunity, 2010, p. 1294-1303.
Rerks-Ngarm et al. "Vaccination with ALVAC and AIDSVAX to Prevent HIV-1 Infection in Thailand" N Engl J Med, 2009; 361: 2209-2220.
Santra et al. Recombinant poxvirus boosting of DNA-primed rhesus monkeys augments peak but not memory T lymphocyte responses, Proc Natl Acad Sci U S A. 2004, 101(30):11088-93.
Scott & Barnett Surface Proteins of Gram-Positive Bacteria and How They Get There, Annu. Rev. Microbiol. 2006. 60:397-423.
Scott & Zahner Pili with strong attachments: Gram-positive bacteria do it differently, Molecular Microbiology (2006) 62(2), 320-330.
Shi et al., (English Abstract) Progress on lactococcus lactis expressing heterologous antigens as live mucosal vaccines Wei Sheng Wu Xue Bao. 2006, 46(4):680-3.
Starks et al., Assembly of CS1 Pili: the Role of Specific Residues of the Major Pilin, CooA, Journal of Bacteriology, 2006, p. 231-239.
Ton-That et al. Assembly of pili on the surface of Corynebacterium diphtheriae, Molecular Microbiology (2003) 50 (4), 1429-1438.
Ton-That et al. Protein sorting to the cell wall envelope of Gram-positive bacteria, Biochimica et Biophysica Acta 1694 (2004) 269-278.
Veazey et al. "Gastrointestinal tract as a major site of CD4+ T cell depletion and viral replication in SIV infection" Science, 1998; 280(5362): 427-431.
Xin et al. "Immunogenicity and protective efficacy of orally administered recombinant Lactococcus lactis expressing surface-bound HIV Env" Blood, 2003; 102: 223-228.
Zahner et al. SipA is Required for Pilus Formation in *Streptococcus pyogenes* Serotype M3, Journal of Bacteriology, 2008, vol. 190, No. 2, p. 527-535.
Extended European Search Report for EP Application No. 13834644.0 dated Feb. 23, 2016.

* cited by examiner

SEQUENCE LISTING

<160> NUMBER OF SEQ ID NOS: 5

<210> SEQ ID NO 1
<211> LENGTH: 1317
<212> TYPE: DNA
<213> ORGANISM: Artificial Sequence
<220> FEATURE:
<223> OTHER INFORMATION: Synthetic

<400> SEQUENCE: 1
ttgcaaaaga gggataaaac caattatgga agcgctaaca acaaacgacg acaaacgacg    60

```
atcggattac tgaaagtatt tttgacgttt gtagctctga taggaatagt agggttttct    120
atcagagcgt tcggagctga agaacaatca gtgccaaata acaaagccc tatagtgcag     180 aacatccagg ggcaaatggt acatcaggcc atatcaccta gaactttaaa tgcatgggta    240
aaagtagtag aagagaaggc tttcagccca gaagtgatac ccatgttttc agcattatca    300
gaaggagcca ccccacaaga tttaaacacc atgctaaaca cagtgggggg acatcaagca    360
gccatgcaaa tgttaaaaga gaccatcaat gaggaagctg cagaatggga tagagtgcat    420
ccagtgcatg cagggcctat tgcaccaggc cagatgagag aaccaagggg aagtgacata    480
gcaggaacta ctagtaccct tcaggaacaa ataggatgga tgacaaataa tccacctatc    540
ccagtaggag aaatttataa aagatggata atcctgggat taaataaaat agtaagaatg    600
tatagcccta ccagcattct ggacataaga caaggaccaa aggaacccct tagagactat    660
gtagaccggt tctataaaac tctaagagcc gagcaagctt cacaggaggt aaaaaattgg    720
atgacagaaa ccttgttggt ccaaaatgcg aacccagatt gtaagactat tttaaaagca    780
ttgggaccag cggctacact agaagaaatg atgacagcat gtcagggagt aggaggaccc    840
ggccataagg caagagtttt gaagttaact atttctaaaa ctgttactgg aactattgca    900
gataagaaaa agaatttaa ctttgaaata catttaaaat cttctgatgg acaagctata    960
agtggaacat atccgacaaa ctctggagaa ctcacagtta cagatggaaa agctaccttc    1020
acattaaagg atggagaatc attgattgtt gaggggctac cttcaggtta ctcttatgaa    1080
attacagaaa cgggtgcttc agattatgag gtaagtgtta atggaaaaaa tgcaccagat    1140
ggaaaagcga cgaaagcctc agttaaggaa gatgagactg tagcttttga aaaccgaaaa    1200
gatcttgtcc caccaactgg tttgacaaca gatggggcta tctatctttg gttgttatta    1260
cttgttccat ttgggttatt ggtttggcta tttggtcgta agggactaa aaaatga      1317
```

<210> SEQ ID NO 2
<211> LENGTH: 438
<212> TYPE: PRT
<213> ORGANISM: Artificial Sequence
<220> FEATURE:
<223> OTHER INFORMATION: Synthetic

<400> SEQUENCE: 2

```
Leu Gln Lys Arg Asp Lys Thr Asn Tyr Gly Ser Ala Asn Asn Lys Arg
1               5                   10                  15

Arg Gln Thr Thr Ile Gly Leu Leu Lys Val Phe Leu Thr Phe Val Ala
            20                  25                  30

Leu Ile Gly Ile Val Gly Phe Ser Ile Arg Ala Phe Gly Ala Glu Glu
        35                  40                  45

Gln Ser Val Pro Asn Lys Ser Pro Ile Val Gln Asn Ile Gln Gly
    50                  55                  60

Gln Met Val His Gln Ala Ile Ser Pro Arg Thr Leu Asn Ala Trp Val
65                  70                  75                  80

Lys Val Val Glu Glu Lys Ala Phe Ser Pro Glu Val Ile Pro Met Phe
                85                  90                  95

Ser Ala Leu Ser Glu Gly Ala Thr Pro Gln Asp Leu Asn Thr Met Leu
            100                 105                 110

Asn Thr Val Gly Gly His Gln Ala Ala Met Gln Met Leu Lys Glu Thr
        115                 120                 125

Ile Asn Glu Glu Ala Ala Glu Trp Asp Arg Val His Pro Val His Ala
    130                 135                 140
```

Gly Pro Ile Ala Pro Gly Gln Met Arg Glu Pro Arg Gly Ser Asp Ile
145                 150                 155                 160

Ala Gly Thr Thr Ser Thr Leu Gln Glu Gln Ile Gly Trp Met Thr Asn
                165                 170                 175

Asn Pro Pro Ile Pro Val Gly Glu Ile Tyr Lys Arg Trp Ile Ile Leu
            180                 185                 190

Gly Leu Asn Lys Ile Val Arg Met Tyr Ser Pro Thr Ser Ile Leu Asp
        195                 200                 205

Ile Arg Gln Gly Pro Lys Glu Pro Phe Arg Asp Tyr Val Asp Arg Phe
210                 215                 220

Tyr Lys Thr Leu Arg Ala Glu Gln Ala Ser Gln Glu Val Lys Asn Trp
225                 230                 235                 240

Met Thr Glu Thr Leu Leu Val Gln Asn Ala Asn Pro Asp Cys Lys Thr
                245                 250                 255

Ile Leu Lys Ala Leu Gly Pro Ala Ala Thr Leu Glu Glu Met Met Thr
            260                 265                 270

Ala Cys Gln Gly Val Gly Gly Pro Gly His Lys Ala Arg Val Leu Lys
        275                 280                 285

Leu Thr Ile Ser Lys Thr Val Thr Gly Thr Ile Ala Asp Lys Lys Lys
290                 295                 300

Glu Phe Asn Phe Glu Ile His Leu Lys Ser Ser Asp Gly Gln Ala Ile
305                 310                 315                 320

Ser Gly Thr Tyr Pro Thr Asn Ser Gly Glu Leu Thr Val Thr Asp Gly
                325                 330                 335

Lys Ala Thr Phe Thr Leu Lys Asp Gly Glu Ser Leu Ile Val Glu Gly
            340                 345                 350

Leu Pro Ser Gly Tyr Ser Tyr Glu Ile Thr Glu Thr Gly Ala Ser Asp
        355                 360                 365

Tyr Glu Val Ser Val Asn Gly Lys Asn Ala Pro Asp Gly Lys Ala Thr
370                 375                 380

Lys Ala Ser Val Lys Glu Asp Glu Thr Val Ala Phe Glu Asn Arg Lys
385                 390                 395                 400

Asp Leu Val Pro Pro Thr Gly Leu Thr Thr Asp Gly Ala Ile Tyr Leu
                405                 410                 415

Trp Leu Leu Leu Leu Val Pro Phe Gly Leu Leu Val Trp Leu Phe Gly
            420                 425                 430

Arg Lys Gly Thr Lys Lys
        435

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
tgactgtgaa cgttcgagat ga                                      22

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

```
Val Pro Pro Thr Gly
1               5
```

<210> SEQ ID NO 5
<211> LENGTH: 328
<212> TYPE: PRT
<213> ORGANISM: Artificial Sequence
<220> FEATURE:
<223> OTHER INFORMATION: Synthetic

<400> SEQUENCE: 5

```
Met Arg Gly Ser His His His His His His Gly Met Ala Ser Met Thr
1               5                   10                  15

Gly Gln Gln Met Gly Arg Asp Leu Tyr Asp Asp Asp Asp Lys Asp Pro
            20                  25                  30

Met Ala Gln Val Ile Asn Thr Asn Ser Leu Ser Leu Thr Gln Asn
        35                  40                  45

Asn Leu Asn Lys Ser Gln Ser Ser Leu Ser Ser Ala Ile Glu Arg Leu
50                  55                  60

Ser Ser Gly Leu Arg Ile Asn Ser Ala Lys Asp Asp Ala Ala Gly Gln
65                  70                  75                  80

Ala Ile Ala Asn Arg Phe Thr Ser Asn Ile Lys Gly Leu Thr Gln Ala
                85                  90                  95

Ser Arg Asn Ala Asn Asp Gly Ile Ser Ile Ala Gln Thr Thr Glu Gly
            100                 105                 110

Ala Leu Asn Glu Ile Asn Asn Asn Leu Gln Arg Val Arg Glu Leu Ser
        115                 120                 125

Val Gln Ala Thr Asn Gly Thr Asn Ser Asp Ser Asp Leu Lys Ser Ile
130                 135                 140

Gln Asp Glu Ile Gln Gln Arg Leu Glu Glu Ile Asp Arg Val Ser Asn
145                 150                 155                 160

Gln Thr Gln Phe Asn Gly Val Lys Val Leu Ser Gln Asp Asn Gln Met
                165                 170                 175

Lys Ile Gln Val Gly Ala Asn Asp Gly Glu Thr Ile Thr Ile Asp Leu
            180                 185                 190

Gln Lys Ile Asp Val Lys Ser Leu Gly Leu Asp Gly Phe Asn Val Asn
        195                 200                 205

Ser Pro Gly Ile Ser Gly Gly Gly Gly Ile Leu Asp Ser Met Gly
210                 215                 220

Thr Leu Ile Asn Glu Asp Ala Ala Ala Lys Lys Ser Thr Ala Asn
225                 230                 235                 240

Pro Leu Ala Ser Ile Asp Ser Ala Leu Ser Lys Val Asp Ala Val Arg
                245                 250                 255

Ser Ser Leu Gly Ala Ile Gln Asn Arg Phe Asp Ser Ala Ile Thr Asn
            260                 265                 270

Leu Gly Asn Thr Val Thr Asn Leu Asn Ser Ala Arg Ser Arg Ile Glu
        275                 280                 285

Asp Ala Asp Tyr Ala Thr Glu Val Ser Asn Met Ser Lys Ala Gln Ile
        290                 295                 300

Leu Gln Gln Ala Gly Thr Ser Val Leu Ala Gln Ala Asn Gln Val Pro
305                 310                 315                 320

Gln Asn Val Leu Ser Leu Leu Arg
            325
```

HIV IMMUNE STIMULATING COMPOSITIONS COMPRISING RECOMBINANTLY EXPRESSED PILI ON BACTERIA AND METHODS RELATED THERETO

CROSS-REFERENCE TO RELATED APPLICATIONS

This application is a division of U.S. patent application Ser. No. 14/422,490 filed Feb. 19, 2015, which is the National Stage of International Application No. PCT/US2013/058383 filed Sep. 6, 2013, which claims the benefit of priority to U.S. Provisional Application No. 61/698,200 filed Sep. 7, 2012. The entirety of each of these applications is hereby incorporated by reference for all purposes.

STATEMENT REGARDING FEDERALLY FUNDED RESEARCH

This invention was made with government support under grant number AI050409 and AI055605 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 13001USDIV_ST25.txt. The text file is 10 KB, was created on Dec. 20, 2017, and is being submitted electronically via EFS-Web.

BACKGROUND

There are millions of humans living with HIV/AIDS. Drugs and improved treatment regimens have successfully prolonged the lives of infected individuals. However, according to the CDC from 2008 through 2011, the annual estimated number and rate of diagnoses of HIV infection remained stable in the United States. Thus, there is a great need to develop a safe and effective HIV vaccine to reduce the spread of HIV infections.

Initial HIV vaccines candidates AIDSVAX BB and AIDSVAX B/E consisted of bivalent gp120 subunits of the viral envelope glycoprotein (Env). These vaccines elicited antibody responses in all of vaccinated participants but it was ineffective in preventing HIV-1 infection or in modifying postinfection markers of disease progression. The MRKAD5 vaccine is an adenovirus 5 (Ad5) vectored encoding Gag, Pol, and Nef. It elicited both HIV specific $CD8^+$ and $CD4^+$ T cell responses in most clinical trial participates but also failed to prevent infection. The ALVAC-HIV (vCP1521) vaccine contains a canary pox vector that encodes Gag, protease, and Env. ALVAC-HIV was studied in combination with AIDSVAX B/E boosts. This combination did not induce measurable $CD8^+$ T cells in most clinical trial participants; however, it did induce antibody and $CD4^+$ T cells and provided some protection against infection. See Rerks-Ngarm et al., N Engl J Med, 2009, 361:2209-2220 and Kintu et al., J Acquir Immune Defic Syndr. 2013, 63(1):1-8.

Veazey et al., report that the gastrointestinal tract is a major site of CD4+ T cell depletion and viral replication in SIV infection. Science, 1998, 280(5362):427-31. Brenchley et al., report that CD4+ T cell depletion occurs during all stages of HIV disease and occurs predominantly in the gastrointestinal tract. J Exp Med, 2004, 200(6):749-59. See also Li et al., Nature, 2005, 434(7037):1148-52 and Mattapallil et al., Nature, 2005, 434(7037):1093-7. Thus, there is a need for HIV vaccines and vaccination methods that protect the lymphoid system in the gastrointestinal tract.

Quigley et al. report a foreign protein incorporated on the tip of T3 pili in *Lactococcus lactis* (*L. lactis*) elicits systemic and mucosal immunity. Infect Immun. 2010, 78(3):1294-303. See also Bahey-El-Din & Gahan, Hum Vaccin, 2011, 7(1):106-9.

Xin et al. report orally administered recombinant *L. lactis* expressing surface-bound HIV Env. Blood, 2003, 102:223-8.

SUMMARY

This disclosure relates to recombinant bacteria, e.g. *L. lactis*, expressing heterologous pili containing human immunodeficiency virus (HIV) antigens. In certain embodiments, the recombinant bacteria are administered in combination with other HIV antigens, nucleic acids encoding HIV antigens, recombinant virus encoding HIV antigens, anti-viral agents and/or adjuvants in an effective amount to elicit a mucosal immune response against the HIV antigen.

In certain embodiments, the disclosure relates to methods for eliciting an immune response against human immunodeficiency virus (HIV), comprising administering a recombinant *L. lactis* bacterium comprising a recombinant nucleic acid encoding an HIV antigen and encoding heterologous proteins capable of forming pili on the *L. lactis* bacterium, wherein *L. lactis* bacterium expresses the HIV antigen on the tip of the pili, to a subject in an effective amount to elicit antibody responses to the HIV antigen in mucosal secretions of the subject.

In certain embodiments, this disclosure relates to methods of eliciting an immune response in a subject to HIV comprising a) enterally administering a priming dose of recombinant *L. lactis* bacterium comprising a recombinant nucleic acid encoding an HIV antigen and encoding heterologous proteins capable of forming pili on the *L. lactis* bacterium, wherein *L. lactis* bacterium expresses the HIV antigen on the tip of the pili, to a subject in an effective amount to elicit antibody responses to the HIV protein in mucosal secretions of the subject, and b) parenterally administering a boosting dose of an HIV antigen, a nucleic acid encoding an HIV antigen, recombinant virus encoding an HIV antigen, or combinations thereof, to the subject in an effective amount to elicit a systemic immune response to the HIV antigen.

In certain embodiments, enterally administering is by mouth, gastric feeding tube, duodenal feeding tube, gastrostomy, or rectally.

In certain embodiments, the HIV antigen is Gag, Pol, Env, Nef, Tat, Rev, Vpu, Vif, Vpr, protease, reverse transcriptase, gp120, gp160, p17, p24, p9, p6, p2, p1, p55, p66, p51, segments, or combinations derived therefrom.

In certain embodiments, the antigen is HIV Gag p24, Env gp120, Env gp41, or gp41 with a 115 amino acid C-terminal truncation or derived therefrom.

In certain embodiments, the proteins capable of forming a pilus are capable of forming a group A *streptococcus* pilus.

In certain embodiments, the nucleic acid comprises genes cpa, sipA2, tee3, and srtC2 from a group A *streptococcus*.

In certain embodiments, parentally administration is by intravenous, intra-arterial, intra-osseous, intra-muscular, or subcutaneous injection or infusion.

In certain embodiments, the immune boosting composition is a recombinant nucleic acid or recombinant virus encoding a second antigen of HIV in operable combination with a promoter wherein the recombinant nucleic acid or recombinant virus are capable of forming a virus like particle. In certain embodiments, the immune boosting composition is a recombinant adenovirus type 5 or modified vaccinia Ankara encoding a second antigen of HIV. In certain embodiments, the second antigen is a viral Gag, Pol, Env, Nef, Tat, Rev, Vpu, protease, reverse transcriptase, mutations, combinations, or segments thereof. In certain embodiments, the antigen is the same or different as the second antigen.

In certain embodiments, this disclosure relates to methods disclosed herein further comprising administering adjuvants in combination with the composition comprising recombinant *L. lactis* bacterium.

In certain embodiments, this disclosure relates to compositions and methods related thereto, wherein recombinant *L. lactis* bacterium further comprises pili wherein the HIV antigen and an adjuvant protein is in the tip of the pilus such as protein adjuvants flagellin and dmLT.

In certain embodiments, the disclosure relates to method disclosed herein further comprising the step of administering a pharmaceutical composition comprising an anti-viral agent to the subject.

In certain embodiments, the disclosure relates to method disclosed herein further comprising the step of administering gp120 subunits of the viral envelope glycoprotein (Env) to the subject.

In certain embodiments, the disclosure relates to compositions comprising genetically engineered gram-positive bacterium comprising a recombinant nucleic acid encoding HIV antigen and encoding heterologous proteins capable of forming pili on the gram-positive bacterium, wherein Gag antigen is expressed on the tip of the pili.

In certain embodiments, the disclosure relates to compositions comprising genetically engineered gram-positive bacterium comprising a recombinant nucleic acid encoding HIV Gag p24 and encoding heterologous proteins capable of forming pili on the gram-positive bacterium, wherein Gag p24 is expressed on the tip of the pili. Typically, the gram-positive bacterium is bacterium *L. lactis*. In certain embodiments, the recombinant nucleic acid encoding HIV Gag p24 is configured between N terminus amino acids of a Cpa protein of a group A *Streptococcus* and C terminus amino acids from the Cpa.

In certain embodiments, the disclosure relates to compositions and methods related thereto comprising recombinant bacteria expressing a polypeptide chimera of Gag p24 and Cpa protein on the tip of the pili having sequence of SEQ ID NO: 2, or those with 60%, 70%, 80%, 90% 95%, or 98% sequence identity thereto.

In certain embodiments, the peptide chimera has 1, 2, 3, 4, 5, 6, 7, 8, or 9 substitutions within SEQ ID NO: 2. In certain embodiments, the substitutions are conserved substitutions. In certain embodiments, the substitutions are not within first 11 amino acids, the cell wall sorting signal (CWSS) or VPPTG (SEQ ID NO: 4).

In certain embodiments, the disclosure relates to compositions and method related thereto comprising a recombinant vector, plasmid, or bacteria comprising a nucleic acid sequence encoding the polypeptide chimera.

In certain embodiments, the disclosure relates to compositions and method related thereto comprising a recombinant vector, plasmid, or bacteria comprising a nucleic acid sequence of SEQ ID NO: 1, or those with 60%, 70%, 80%, 90% or 95% sequence identity thereto.

DETAILED DISCUSSION

Figure 1:
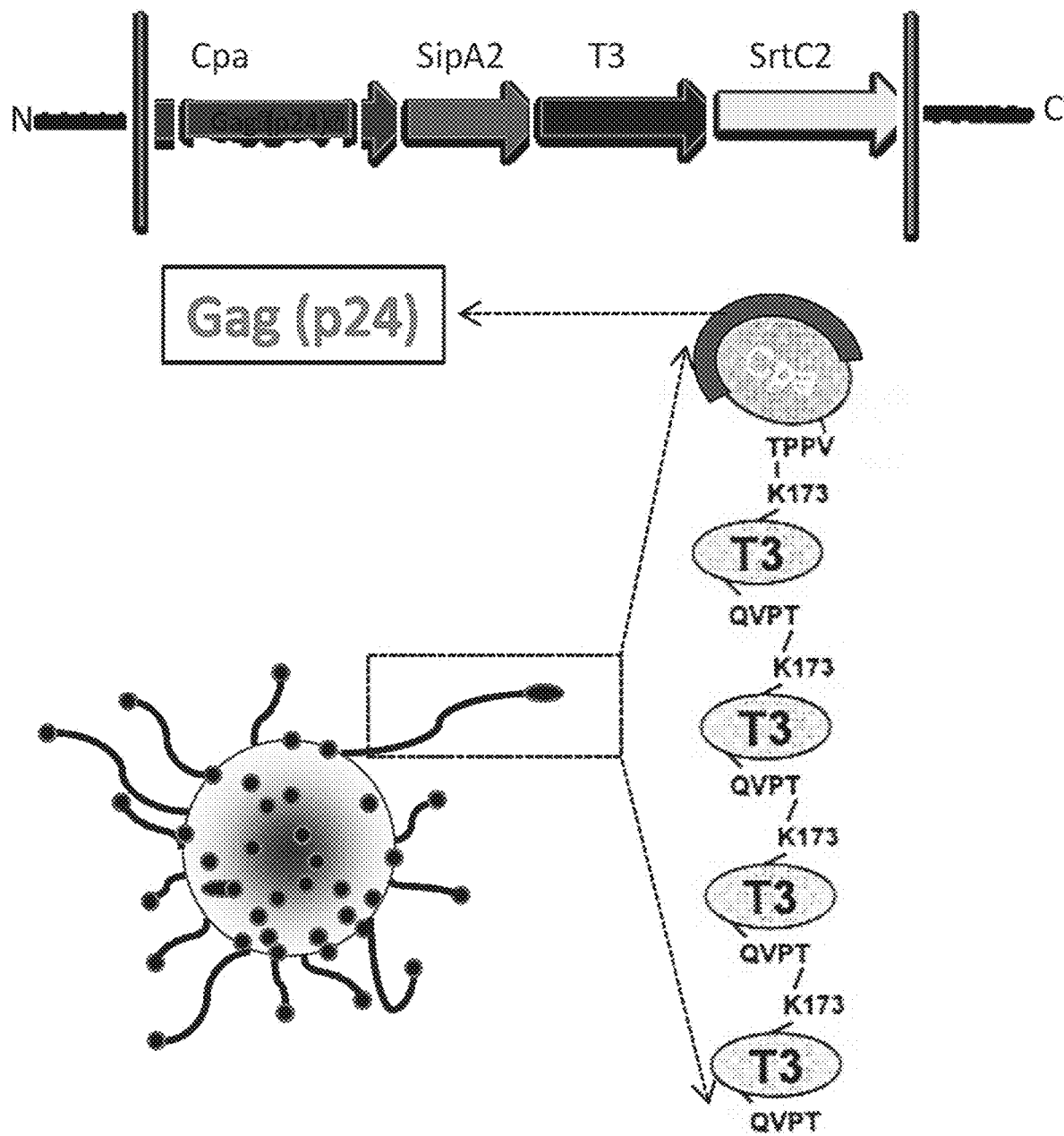
FIG. 1 shows a diagram illustrating FCT locus from group A *Lactococcus* (cpa, sipA, srtC2 and tee3), cloning of Gag (p24) into a genetic locus off GAS pilus, sub-cloned into pJRS vector, and transformed to *L. Lactis* cells and pilus formation. T3 pili on the surface of *L. lactis* show the motif preceding the hydrophobic domain of the CWSS of each pili protein.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "subject" refers to any animal, typically a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

The terms "protein" and "polypeptide" refer to compounds comprising amino acids joined via peptide bonds and are used interchangeably. Where "amino acid sequence" is recited herein, it to refer to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycolsylations and addition of lipid moieties.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.).

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long.

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a polynucleotide having a nucleotide sequence encoding a gene" or "a polynucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The skilled artisan will further appreciate that changes (i.e. one or more deletions, additions and/or substitutions of one or more amino acid) can be introduced by mutation using classic or recombinant techniques to effect random or targeted mutagenesis. A suitable variant in use in the present disclosure typically has an amino acid sequence having a high degree of homology with the amino acid sequence of the corresponding HIV antigen. In one embodiment, the amino acid sequence of the HIV antigen of the disclosure is at least 70%, at least about 75%, at least about 80%, at least about 90%, typically at least about 95%, more typically at least about 97% and even more typically at least about 99% identical to the corresponding native sequence.

Percent identities between nucleic acid or amino acid sequences can be determined using standard methods known to those of skill in the art. For instance, for determining the percentage of homology between two amino acid sequences, the sequences are aligned for optimal comparison purposes. The amino acid residues at corresponding amino acid positions are then compared. Gaps can be introduced in one or both amino acid sequence(s) for optimal alignment and non-homologous sequences can be disregarded for comparison purposes. When a position in the first sequence is occupied by the same amino acid residue as the corresponding position in the second sequence, then the sequences are identical at that position. The percent identity between the two sequences is a function of the number of identical positions shared by the sequences, taking into account the number of gaps which need to be introduced for optimal alignment and the length of each gap. The comparison of sequences and determination of percent identity and similarity between two sequences can be accomplished using a mathematical algorithm. Moreover, various computer programs are available to determine percentage identities between amino acid sequences and between nucleic acid sequences, such as GCG™ program (available from Genetics Computer Group, Madison, Wis.), DNAsis™ program (available from Hitachi Software, San Bruno, Calif.) or the MacVector™ program (available from the Eastman Kodak Company, New Haven, Conn.). Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The disclosure encompasses variants of the above-described nucleic acid molecules of the disclosure e.g., that encode variants of the HIV antigens that are described. The variation(s) encompassed by the present disclosure can be created by introducing one or more nucleotide substitutions, additions and/or deletions into the nucleotide sequence by standard techniques, such as site-directed mutagenesis and PCR-mediated mutagenesis. Following mutagenesis, the variant nucleic acid molecule can be expressed recombinantly as described herein and the activity of the resulting protein can be determined using, for example, assays described herein.

The nucleic acid molecule of SEQ ID NO:1 can be altered to provide preferential codon usage for a specific host cell. The disclosure further encompasses nucleic acid molecules that differ due to the degeneracy of the genetic code and thus encode for example the same HIV antigen as SEQ ID NO: 2.

The term "derived from" or "derivative" in relation to the HIV antigens included in the invention means that the antigens may have been altered in a limited way compared to their native counterparts. This includes point mutations which may change the properties of the protein for example by improving expression in prokaryotic systems or removing undesirable activity including undesirable enzyme activity. However, the antigens must remain sufficiently similar to the native antigens such that they retain the antigenic properties desirable in a vaccine and thus they remain capable of raising an immune response against the native antigen. Whether or not a particular derivative raises such an immune response may be measured by a suitable immunological assay such as an ELISA (for antibody responses) or flow cytometry using suitable staining for cellular markers and cytokines (for cellular responses).

Immunogenic segments as described herein will contain at least one epitope of the antigen and display HIV antigenicity and are capable of raising an immune response when presented in a suitable construct, e.g., in the tip of the pili as a chimera of the Csp protein, such as for example when fused to other HIV antigens or protein adjuvants, the immune response being directed against the native antigen. Typically the immunogenic segments contain at least 20, preferably 50, more preferably 100 contiguous amino acids from the HIV antigen.

HIV Antigens

It is contemplated that HIV antigen may be selected from Gag, Pol, Env, Nef, Tat, Rev, Vpu, Vif, Vpr, protease, reverse transcriptase (RT), gp120, gp160, p17, p24, p9, p6, p2, p1, p55, p66, p51, or any protein sequence generated by the HIV genome, segments, or combinations derived therefrom. In certain embodiments, the antigen is HIV Gag p24, Env gp120, Env gp41, or gp41 with a 115 amino acid C-terminal truncation.

HIV-1 is an RNA virus of the family Retroviridae. The HIV genome encodes at least nine proteins which are divided into three classes: the major structural proteins Gag, Pol and Env, the regulatory proteins Tat and Rev, and the accessory proteins Vpu, Vpr, Vif and Nef. The HIV genome exhibits the 5'LTR-gag-pol-env-LTR3' organization typical of retroviruses.

The HIV envelope glycoprotein gp120 is the viral protein that is used for attachment to the host cell. This attachment is mediated by binding to two surface molecules of helper T cells and macrophages, known as CD4 and one of the two chemokine receptors CCR-5 or CXCR-4. The gp120 protein is first expressed as a larger precursor molecule (gp160), which is then cleaved post-translationally to yield gp120 and gp41. The gp120 protein is retained on the surface of the virion by linkage to the gp41 molecule, which is inserted into the viral membrane.

The gp120 protein is the principal target of neutralizing antibodies, but unfortunately the most immunogenic regions of the proteins (V3 loop) are also the most variable parts of the protein. The gp120 protein contains epitopes that are typically recognized by cytotoxic T lymphocytes (CTL). These effector cells are able to eliminate virus-infected cells, and therefore constitute a second major antiviral immune mechanism. In contrast to the target regions of neutralizing antibodies, some CTL epitopes appear to be relatively conserved among different HIV strains. For this reason gp120 and gp160 may be useful antigenic components in vaccines that aim at eliciting cell-mediated immune responses.

Non-envelope proteins of HIV-1 include for example internal structural proteins such as the products of the gag and pol genes and other non-structural proteins such as Rev, Nef, Vif, Vpu, and Tat.

The Gag gene is translated as a precursor polypeptide that is cleaved by protease to yield products that include the matrix protein (p17), the capsid (p24), the nucleocapsid (p9), p6 and two space peptides, p2 and p1. The Gag gene gives rise to the 55-kilodalton (kD) Gag precursor protein, also called p55, which is expressed from the unspliced viral mRNA. During translation, the N terminus of p55 is myristoylated, triggering its association with the cytoplasmic face of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the pol gene) during the process of viral maturation into four smaller proteins designated MA (matrix [p17]), CA (capsid [p24]), NC (nucleocapsid [p9]), and p6. In addition to the 3 major Gag proteins, Gag precursors contain several other regions, which are cleaved out and remain in the virion as peptides of various sizes. These proteins have different roles e.g. the p2 protein has a proposed role in regulating activity of the protease and contributes to the correct timing of proteolytic processing.

The p17 (MA) polypeptide is derived from the N-terminal, myristoylated end of p55. Most MA molecules remain attached to the inner surface of the virion lipid bilayer, stabilizing the particle. A subset of MA is recruited inside the deeper layers of the virion where it becomes part of the complex which escorts the viral DNA to the nucleus. These MA molecules facilitate the nuclear transport of the viral genome because a karyophilic signal on MA is recognized by the cellular nuclear import machinery. This phenomenon allows HIV to infect non-dividing cells, an unusual property for a retrovirus.

The p24 (CA) protein forms the conical core of viral particles. Cyclophilin A has been demonstrated to interact with the p24 region of p55 leading to its incorporation into HIV particles. The interaction between Gag and cyclophilin A is essential because the disruption of this interaction by cyclosporin A inhibits viral replication.

The NC region of Gag is responsible for specifically recognizing the so-called packaging signal of HIV. The packaging signal consists of four stem loop structures located near the 5' end of the viral RNA, and is sufficient to mediate the incorporation of a heterologous RNA into HIV-1 virions. NC binds to the packaging signal through interactions mediated by two zinc-finger motifs. NC also facilitates reverse transcription.

The p6 polypeptide region mediates interactions between p55 Gag and the accessory protein Vpr, leading to the incorporation of Vpr into assembling virions. The p6 region also contains a so-called late domain which is required for the efficient release of budding virions from an infected cell.

The Pol gene encodes two proteins containing the two activities needed by the virus in early infection, the reverse transcriptase (RT) and the integrase protein needed for integration of viral DNA into cell DNA. The primary product of Pol is cleaved by the virion protease to yield the amino terminal RT peptide which contains activities necessary for DNA synthesis (RNA and DNA-dependent DNA polymerase activity as well as an RNase H function) and carboxy terminal integrase protein. HIV RT is a heterodimer of full-length RT (p66) and a cleavage product (p51) lacking the carboxy terminal RNase H domain.

RT is one of the most highly conserved proteins encoded by the retroviral genome. Two major activities of RT are the DNA Polymerase (Pol) and Ribonuclease H. The DNA Pol activity of RT uses RNA and DNA as templates interchangeably and like all DNA polymerases known is unable to initiate DNA synthesis de novo, but requires a preexisting molecule to serve as a primer (RNA). The RNase H activity inherent in all RT proteins plays the essential role early in replication of removing the RNA genome as DNA synthesis proceeds. It selectively degrades the RNA from all RNA-DNA hybrid molecules. Structurally the polymerase and RNase H occupy separate, non-overlapping domains with the Pol covering the amino two thirds of the Pol gene. The p66 catalytic subunit is folded into 5 distinct subdomains. The amino terminal 23 of these have the portion with RT activity. Carboxy terminal to these is the RNase H Domain.

Nucleic Acids Encoding HIV Antigens, Recombinant Viruses Encoding HIV Antigens

In certain embodiments, the disclosure relates to nucleic acids encoding the polypeptides that are HIV antigens. The nucleic acids may be used as nucleic acid vaccines. The nucleic acids may be present within any of a variety of delivery systems known to those of ordinary skill in the art, including nucleic acid expression systems such as plasmid DNA, bacterial and viral expression systems. Numerous gene delivery techniques are well known in the art, such as those described by Rolland, Crit. Rev. Therap. Drug Carrier Systems 15:143-198, 1998 and references cited therein. Appropriate nucleic acid expression systems contain the necessary DNA sequences for expression in the patient (such as a suitable promoter and terminating signal). When the expression system is a recombinant live microorganism, such as a virus or bacterium, the gene of interest can be inserted into the genome of the live recombinant virus or bacterium. Inoculation and in vivo infection with this live vector will lead to in vivo expression of the HIV antigen and induction of immune responses.

Viruses and bacteria used for this purpose are for instance: poxviruses (e.g; vaccinia, fowlpox, canarypox, modified poxviruses e.g. Modified Virus Ankara (MVA)), alphaviruses (Sindbis virus, Semliki Forest Virus, Venezuelian Equine Encephalitis Virus), flaviviruses (yellow fever virus, Dengue virus, Japanese encephalitis virus), adenoviruses, adeno-associated virus, picornaviruses (poliovirus, rhinovirus), herpesviruses (varicella zoster virus, etc), morbilliviruses (e.g. measles), *Listeria, Salmonella, Shigella, Neisseria*. These viruses and bacteria can be inactivated (dead virus), or attenuated in various ways in order to obtain live vaccines.

In certain embodiments, an adenovirus for use as a live vector is a low sero-prevalent human adenovirus such as Ad5 or Ad35 or a non-human originating adenovirus such as a non-human primate adenovirus such as a simian adenovirus. Such low sero-prevalent human or similar adenoviruses will have less than 60%, typically less than 50% seroprevalence in the population. Typically, the vectors are replication defective. Typically these viruses contain an E1 deletion and can be grown on cell lines that are transformed with an E1 gene.

In certain embodiments, the disclosure contemplates the use of simian adenoviruses viruses isolated from chimpanzee. In certain embodiments, the simian adenoviruses may be C68 (also known as Pan 9) (See U.S. Pat. No. 6,083,716) and Pan 5, 6 and Pan 7 (WO 03/046124). These vectors can be manipulated to insert a heterologous nucleic acid such that the polypeptides of HIV antigens maybe expressed. The use, formulation and manufacture of such recombinant adenoviral vectors is described in detail in WO 03/046142.

In certain embodiments, the HIV antigen, e.g., Gag, Pol, Env, Nef, Tat, Rev, Vpu, Vif, Vpr, protease, reverse transcriptase, gp120, gp160, p17, p24, p9, p6, p2, p1, p55, p66, p51, segments, or combinations such as the Nef, p17 and p24 Gag and RT, in a vaccine is in the form of a nucleic acid encoding the desired HIV antigen. Nucleic acids may be used to express the encoded polypeptides in a selected expression system. At least one of the HIV antigens, for example the Gag p24, may be encoded by a codon optimized sequence in the nucleic acid, that is to say the sequence has been optimized for expression in the pili.

The HIV antigens and nucleic acids may be combined with other antigens or nucleic acids encoding other antigens. In particular, this may include HIV env proteins or fragments or derivatives thereof. Typical forms of Env are gp120, gp140 and gp160. The Env may be for example the envelope protein described in WO 00/07631 from an HIV-1 Glade B envelope clone known as R2, or a fragment or derivative thereof.

In certain embodiments, the disclosure relates to a composition comprising any of the HIV antigens or nucleic acids compositions disclosed herein, together with an HIV Env protein or fragment or derivative thereof. In certain embodiments, the disclosure relates to a composition comprising a nucleic acid encoding an HIV antigen and a nucleic acid encoding an HIV Env protein or fragment or derivative thereof.

Methods Eliciting an Immune Response Against Human Immunodeficiency Virus (HIV)

In certain embodiments, the disclosure contemplates methods for eliciting an immune response against human immunodeficiency virus (HIV), comprising administering a priming dose of recombinant *L. lactis* bacterium comprising a recombinant nucleic acid encoding an HIV antigen and encoding heterologous proteins capable of forming pili on the *L. lactis* bacterium, wherein *L. lactis* bacterium expresses the HIV antigen on the tip of the pili, to a subject in an effective amount to elicit antibody responses to the HIV antigen in mucosal secretions of the subject.

In certain embodiments, the disclosure relates to methods for eliciting an immune response against human immunodeficiency virus (HIV), comprising:

a) enterally administering a priming dose of recombinant *L. lactis* bacterium comprising a recombinant nucleic acid encoding an HIV antigen and encoding heterologous proteins capable of forming pili on the *L. lactis* bacterium, wherein *L. lactis* bacterium expresses the HIV antigen on the tip of the pili, to a subject in an effective amount to elicit antibody responses to the HIV protein in mucosal secretions of the subject, and b) parenterally administering a boosting dose of an HIV antigen, a nucleic acid encoding an HIV antigen, recombinant virus encoding an HIV antigen, or combinations thereof, to the subject in an effective amount to elicit a systemic immune response to the HIV antigen.

Methods disclosed herein may be used for vaccination, prophylactic, or therapeutic immunization against HIV.

In certain embodiments, the disclosure relates to the use of the compositions as described herein, in the manufacture of a vaccine for prophylactic or therapeutic immunization against HIV.

The methods disclosed herein contemplate administering recombinant *L. lactis* bacterium comprising a recombinant nucleic acid encoding an HIV antigen and encoding heterologous proteins capable of forming pili on the *L. lactis* bacterium, wherein *L. lactis* bacterium expresses the HIV antigen on the tip of the pili, in combination with an adjuvant, e.g., in the formulation. Suitable adjuvants include an aluminium salt such as aluminium hydroxide or aluminium phosphate, but may also be a salt of calcium, iron or zinc, or may be an insoluble suspension of acylated tyrosine, or acylated sugars, cationically or anionically derivatised polysaccharides, or polyphosphazenes.

Recombinant *L. lactis* bacterium comprising a recombinant nucleic acid encoding an HIV antigen and encoding heterologous proteins capable of forming pili on the *L. lactis* bacterium, wherein *L. lactis* bacterium expresses the HIV antigen on the tip of the pili, may be formulated with adjuvants suitable for use in methods disclosed herein include and are not restricted to the following; double mutant *E. coli* heat-labile toxin (dmLT or LT(R192G/L211A)), a flagellin (TLR5 ligand), and CpG (TLR9 ligand).

As used herein, "a flagellin" refers to the monomer subunit in flagella, e.g., flagellin gene product of FliC and FljB in *S. typhimurium* and FlaA in *L. pneumophila*, or variants, analogs, homologs, derivatives, fragments or combination thereof, such as a domain or polypeptide sequence in the domain. Typically, the flagellin monomer contains D0, D1, D2, and D3 domains. An alignment of the amino acid sequences from different Gram-negative species shows a high degree of similarity in the amino and carboxy terminal domains. The central regions of these proteins may be quite divergent. It is believed that flagellin is responsible for interaction with TLR5 is found in the D1 domain. Smith, K. D., et al, Nature Immunol. (2003) 4:1247-1253 disclose that TLR5 recognizes a site on the flagellin of *Salmonella typhimurium* (FliC) composed of N-terminal residues 78-129 and 135-173 and C-terminal residues 395-444. The term "a flagellin" is not intended to be limited to any particular amino acid sequence provided that it has some homology to known flagellin sequences and the molecule retains the ability to stimulate innate immune responses. The innate immune responses of flagellin are known to include cytokine production in response to TLR (including TLR5) activation and activation of Caspase-1 and IL-1β secretion in response to certain NLRs (including Ipaf). In certain embodiments, a flagellin is contemplated to include additional amino acids within the sequence, such as in the case of fusion or chimeric proteins, provided that these proteins continue to affect an innate immune response that comprises a TLR5-mediated immune response, an Ipaf-mediated immune response or both.

Also specifically contemplated are fragments, variants, analogs, homologs, or derivatives of said flagellin, and combinations thereof provided these molecules continue to affect an innate immune response that comprises a TLR5-mediated immune response, an Ipaf-mediated immune response or both. A flagellin may be isolated from natural sources, by synthetic or recombinant technologies or combinations thereof.

Combination of fragments of flagellin include SEQ ID NO: 5, Met Arg Gly Ser His His His His His His Gly Met Ala Ser Met Thr1 Gly Gln Gln Met Gly Arg Asp Leu Tyr Asp Asp Asp Lys Asp Pro Met Ala Gln Val Ile Asn Thr Asn Ser Leu Ser Leu Leu Thr Gln Asn Asn Leu Asn Lys Ser Gln Ser Ser Leu Ser Ser Ala Ile Glu Arg Leu Ser Ser Gly Leu Arg Ile Asn Ser Ala Lys Asp Asp Ala Ala Gly Gln Ala Ile Ala Asn Arg Phe Thr Ser Asn Ile Lys Gly Leu Thr Gln Ala Ser Arg Asn Ala Asn Asp Gly Ile Ser Ile Ala Gln Thr Thr Glu Gly Ala Leu Asn Glu Ile Asn Asn Asn Leu Gln Arg Val Arg Glu Leu Ser Val Gln Ala Thr Asn Gly Thr Asn Ser Asp Ser Asp Leu Lys Ser Ile Gln Asp Glu Ile Gln Gln Arg Leu Glu Glu Ile Asp Arg Val Ser Asn Gln Thr Gln Phe Asn Gly Val Lys Val Leu Ser Gln Asp Asn Gln Met Lys Ile Gln Val Gly Ala Asn Asp Gly Glu Thr Ile Thr Ile Asp Leu Gln Lys Ile Asp Val Lys Ser Leu Gly Leu Asp Gly Phe Asn Val Asn Ser Pro Gly Ile Ser Gly Gly Gly Gly Gly Ile Leu Asp Ser Met Gly Thr Leu Ile Asn Glu Asp Ala Ala Ala Ala Lys Lys Ser Thr Ala Asn Pro Leu Ala Ser Ile Asp Ser Ala Leu Ser Lys Val Asp Ala Val Arg Ser Ser Leu Gly Ala Ile Gln Asn Arg Phe Asp Ser Ala Ile Thr Asn Leu Gly Asn Thr Val Thr Asn Leu Asn Ser Ala Arg Ser Arg Ile Glu Asp Ala Asp Tyr Ala Thr Glu Val Ser Asn Met Ser Lys Ala Gln Ile Leu Gln Gln Ala Gly Thr Ser Val Leu Ala Gln Ala Asn Gln Val Pro Gln Asn Val Leu Ser Leu Leu Arg. This protein is also known as CBLB502 (AA') as provided for in U.S. Published Patent Application No. 2009/0011982 hereby incorporated by reference.

Other contemplated antigens include, monophosphoryl lipid A, in particular 3-de-O-acylated monophosphoryl lipid A (3D-MPL). 3D-MPL is often supplied as a mixture of 3-de-O-acylated monophosphoryl lipid A with either 4, 5, or 6 acylated chains. Other purified and synthetic lipopolysaccharides have been described (U.S. Pat. No. 6,005,099). A typical form of 3D-MPL is in the form of a particulate formulation having a small particle size less than 0.2 μm in diameter.

Saponins are also contemplated Th1 immunostimulants. For example, Quil A (derived from the bark of the South American tree Quillaja *Saponaria* Molina), and fractions thereof, are described in U.S. Pat. No. 5,057,540. The haemolytic saponins QS21 and QS17 (HPLC purified fractions of Quil A) have been described as potent systemic adjuvants, and the method of their production is disclosed in U.S. Pat. No. 5,057,540. Also described in these references is the use of QS7 (a non-haemolytic fraction of Quil-A) which acts as a potent adjuvant for systemic vaccines. Combinations of QS21 and polysorbate or cyclodextrin are also contemplated (WO 99/10008). Particulate adjuvant systems comprising fractions of QuilA, such as QS21 and QS7 are described in WO 96/33739 and WO 96/11711.

In certain embodiments, the adjuvant is an immunostimulatory oligonucleotide containing unmethylated CpG dinucleotides ("CpG"). CpG is an abbreviation for cytosine-guanosine dinucleotide motifs present in DNA (WO 96/02555). Certain palindromic sequences, including a central CG motif, carried this activity. See Krieg, Nature 374, p 546 1995. The CG motif is in a certain sequence context common in bacterial DNA but are rare in vertebrate DNA. The immunostimulatory sequence is often: Purine, Purine, C, G, pyrimidine, pyrimidine; wherein the CG motif is not methylated, but other unmethylated CpG sequences are known to be immunostimulatory. In certain embodiments, a contemplated immunostimulatory CpG is TGACTGT-GAACGTTCGAGATGA (SEQ ID NO: 3). CpG may be generally administered in free solution together with the HIV antigens, nucleic acids encoding HIV antigens, recombinant virus encoding HIV antigens or covalently conjugated to an HIV antigen (WO 98/16247), or formulated with a carrier such as aluminum hydroxide.

The adjuvants as described above may be formulated together with carriers, such as for example liposomes, oil in water emulsions, and or metallic salts, including aluminum salts (such as aluminum hydroxide). For example, 3D-MPL may be formulated with aluminum hydroxide or oil in water emulsions; QS21 may be advantageously formulated with cholesterol containing liposomes, oil in water emulsions or alum; CpG may be formulated with alum or with other cationic carriers.

Combinations of adjuvants are also contemplated, e.g., a combination of a monophosphoryl lipid A and a saponin derivative, the combination of QS21 and 3D-MPL, or a combination of CpG plus a saponin such as QS21. Alternatively. the saponin may be formulated in a liposome. In certain embodiments, an adjuvant system comprises a combination of monophosphoryl lipid A, preferably 3D-MPL, together with an aluminium salt. In certain embodiments, an adjuvant system comprises QS21, 3D-MPL & tocopherol in an oil in water emulsion. In certain embodiments, an adjuvant system comprises a CpG oligonucleotide alone or together with an aluminum salt.

Administration of the pharmaceutical composition comprising recombinant L. lactis bacterium comprising a recombinant nucleic acid encoding an HIV antigen and encoding heterologous proteins capable of forming pili on the L. lactis bacterium, wherein L. lactis bacterium expresses the HIV antigen on the tip of the pili, may take the form of one or of more than one individual dose, for example as repeat doses of the same polypeptide containing composition, or in a heterologous "prime-boost" vaccination regime. A heterologous prime-boost regime uses administration of different forms of vaccine in the prime and the boost, each of which may itself include two or more administrations. The priming composition and the boosting composition will have at least one antigen in common, although it is not necessarily an identical form of the antigen, it may be a different form of the same antigen.

Prime-boost immunizations may be performed with recombinant L. lactis bacterium comprising a recombinant nucleic acid encoding an HIV antigen and encoding heterologous proteins capable of forming pili on the L. lactis bacterium, wherein L. lactis bacterium expresses the HIV antigen on the tip of the pili, in combination with a protein and DNA-based formulations. Such a strategy is considered to be effective in inducing broad immune responses.

A schedule for vaccination may comprise the sequential ("prime-boost") or simultaneous administration of recombinant L. lactis bacterium comprising a recombinant nucleic acid encoding an HIV antigen and encoding heterologous proteins capable of forming pili on the L. lactis bacterium, wherein L. lactis bacterium expresses the HIV antigen on the tip of the pili, in combination with HIV antigens and/or DNA encoding the HIV antigen. The DNA may be delivered as naked DNA such as plasmid DNA or in the form of a recombinant live vector, e.g. a poxvirus vector, an adenovirus vector, a measles virus vector or any other suitable live vector. Recombinant L. lactis bacterium comprising a recombinant nucleic acid encoding an HIV antigen and encoding heterologous proteins capable of forming pili on the L. lactis bacterium, wherein L. lactis bacterium expresses the HIV antigen on the tip of the pili, and HIV antigens may be injected once or several times followed by one or more DNA administrations, or DNA may be used first for one or more administrations followed by one or more recombinant L. lactis bacterium comprising a recombinant nucleic acid encoding an HIV antigen and encoding heterologous proteins capable of forming pili on the L. lactis bacterium, wherein L. lactis bacterium expresses the HIV antigen on the tip of the pili, and protein immunizations.

One example of a contemplated prime-boost immunization involves priming with recombinant L. lactis bacterium comprising a recombinant nucleic acid encoding an HIV antigen and encoding heterologous proteins capable of forming pili on the L. lactis bacterium, wherein L. lactis bacterium expresses the HIV antigen on the tip of the pili, followed by boosting with a DNA in the form of a recombinant live vector such as a modified poxvirus vector, for example Modified Virus Ankara (MVA) or an alphavirus, for example Venezuelian Equine Encephalitis Virus, or an adenovirus vector, or a measles virus vector, or boosting with an HIV protein, preferably an adjuvanted protein.

Both the priming composition and the boosting composition may be delivered in more than one dose. Furthermore, the initial priming and boosting doses may be followed up with further doses which may be alternated to result.

In certain embodiments, this disclosure relates to the co-administration of priming or boosting compositions with orally administering recombinant bacteria that present HIV antigens on pilus, typically through the expression of an HIV antigen with the Cpa chimera.

In certain embodiments, contemplated priming or boosting compositions in combination with recombinant bacteria that present HIV antigens on pilus include a recombinant glycoprotein 120 antigen absorbed to alum such as AIDS-VAX B/B. See Flynn et al., J Infect Dis 2005; 191:654-65.

In certain embodiments, priming or boosting compositions include a recombinant adenovirus Ad5 or Ad6 encoding one or more HIV antigens such as MRKAd HIV-1 nef-gag-pol. See Harro et al., Clin Vaccine Immunol, 16 (9): 1285.

In one example the priming or boosting composition is J57. The recombinant vector, pGA2/JS7 DNA (JS7), is an HIV-1 DNA vaccine that produces non-infectious virus-like particles (VLPs). It encodes HIV-1$_{HXB-2}$ Gag, HIV-1$_{BH10}$, protease (PR) and reverse transcriptase (RT), and Env, Tat, Rev, and Vpu derived from the HXB-2 and ADA strains of HIV-1. See Smith et al. AIDS Res Hum Retroviruses, 2004, 20:1335-47 and Smith et al., AIDS Res Hum Retroviruses, 2004, 20:654-65.

In one example, the priming or boosting composition is modified vaccinia virus Ankara encoding HIV antigens such as MVA62. Modified vaccinia virus Ankara (MVA) MVA/HIV62 (MVA62) produces noninfectious virus-like particles (VLP). It also encodes HIV-1 Gag, PR, RT, and env. MVA62 contains the RT but not the Gag and PR mutations of JS7. The ADA Env gene is truncated by 115 C-terminal amino acids of gp41. See Wyatt et al., AIDS Res Hum Retroviruses, 2004, 20:645-53, Wyatt et al., Vaccine 2008; 26:486-93, and Wyatt et al., Virology 2008; 372:260-72.

In one example the priming or boosting composition is a canarypox (ALVAC) vector encoding HIV antigens such as vCP125 encoding Env (gp160), vCP205 encoding Env (gp120, TM gp41), Gag, and Pol, vCP300 encoding Env (gp120, TM gp41), gag, pol, CTL epitopes in pol and nef, and vCP1433 encoding Env (gp120, TM gp41), gag, pol, CTL epitopes in pol and nef. See Bruyn et al., Vaccine, 2004, 22(5-6):704-713.

In certain embodiments, the disclosure contemplates a pharmaceutical kit comprising: a) a composition comprising recombinant L. lactis bacterium comprising a recombinant nucleic acid encoding an HIV antigen and encoding heterologous proteins capable of forming pili on the L. lactis bacterium, wherein L. lactis bacterium expresses the HIV antigen on the tip of the pili, together with a pharmaceutically acceptable excipient; and b) a composition comprising a DNA in the form of a recombinant live vector such as a modified poxvirus vector, for example Modified Virus Ankara (MVA) or an alphavirus, for example Venezuelian Equine Encephalitis Virus, or an adenovirus vector, or a measles virus vector, or a composition with an HIV protein, preferably an adjuvanted protein, together with a pharmaceutically acceptable excipient.

In certain embodiments, the disclosure contemplates methods for eliciting an immune response against human immunodeficiency virus (HIV), comprising administering a priming dose of recombinant L. lactis bacterium comprising a recombinant nucleic acid encoding an HIV antigen and encoding heterologous proteins capable of forming pili on the L. lactis bacterium, wherein L. lactis bacterium expresses the HIV antigen on the tip of the pili, to a subject in an effective amount to elicit antibody responses to the HIV antigen in mucosal secretions of the subject and in combination with an anti-viral agent.

In certain embodiments, the anti-viral agent is selected from abacavir, acyclovir, acyclovir, adefovir, amantadine, amprenavir, ampligen, arbidol, atazanavir, atripla, boceprevir, cidofovir, combivir, complera, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, stribild, tenofovir, tenofovir disoproxil, tenofovir alafenamide fumarate (TAF), tipranavir, trifluridine, trizivir, tromantadine, truvada, valaciclovir, valganciclovir, vicriviroc, vidarabine, viramidine, zalcitabine, zanamivir, zidovudine, or salts and combinations thereof.

In certain embodiments, contemplated combinations include a) zidovudine and nevirapine or salts thereof; b) emtricitabine, tenofovir, and efavirenz or salts thereof; c) emtricitabine, tenofovir and raltegravir or salts thereof; d) emtricitabine, tenofovir, ritonavir and darunavir or salts thereof; or e) emtricitabine, tenofovir, ritonavir, and atazanavir or salts thereof.

Enhancing Induction of HIV-Specific Humoral and Cellular Immunity in Intestinal Mucosa The majority of HIV infections occur via mucosal routes worldwide. Thus, in certain embodiments, this disclosure contemplates a vaccination approach that enhances induction of HIV-specific humoral and cellular immunity in intestinal mucosa in addition to systemic compartments through a prime-boost method. It is believed that vaccines that elicit strong HIV-specific immunity at the mucosal tissue will restrict virus replication very early at the site of virus exposure and thus enhance protection from mucosal infection. HIV vaccines delivered via the intramuscular route typically do not generate high magnitude and long-lived mucosal immune responses.

In certain embodiments, the disclosure contemplates use of a recombinant bacterium L. lactis expressing viral antigens such as HIV proteins on a pilus derived from a group A Streptococcus as an oral vaccine vector to prime immune responses at the intestinal mucosa. A Lactococcus vaccine vector naturally withstands stomach acids and bile, survives temporarily in the intestinal tract, it does not colonize humans, and it does not require a cold chain.

Preliminary results in mice indicate that oral immunization with a recombinant L. lactis expressing HIV-1 Gag p24 on the tip of pilus (LL/Gag) (SEQ ID NO: 2) elicits strong IgG and IgA responses in mucosal secretions and serum. In addition, combining oral rLL/Gag immunizations with an intramuscular boost with recombinant modified vaccinia Ankara expressing HIV Gag (MVA/Gag) generated a robust systemic and intestinal Gag-specific CD8 T cell responses.

In a preliminary study data indicate that four monthly immunizations with rLL/Gag elicits a strong Gag-specific CD4 T cell responses in the rectum. In certain embodiments, the disclosure contemplates L. lactis as a vector for priming strong anti-HIV mucosal immunity that is optionally boosted by viral vectors such as MVA. Oral immunization with L. lactis elicits strong mucosal antibody responses but weak T cell responses. Intramuscular immunization with MVA vaccine elicits strong systemic T cell responses but weak mucosal T and B cell responses. Combining oral L. lactis prime with intramuscular MVA boost elicits strong mucosal and systemic cellular and humoral immunity that is desirable for an effective HIV vaccine.

The prime-boost concept employs recombinant bacteria prime together with viral vector boost and/or soluble envelope subunit boost inducing both $CD4^+$ and $CD8^+$ T cell as well as binding and neutralizing antibody immune responses. An effective immune response will likely comprise a combination of antibodies and $CD4^+$ and $CD8^+$ T cells that recognize, neutralize and/or destroy strains of HIV before an infection becomes irreversibly established.

In certain embodiments, this disclosure also contemplates vaccines capable of reducing viral replication after infection (T cell vaccines). Control of viral replication slows the rate of disease progression and/or reduces transmission of HIV from infected vaccine recipient to partner. The immune stimulating compositions disclosed herein may be administered in combination with anti-viral agents to treat already infected subjects.

IL-17 producing CD4 T cells (Th17) regulate the permeability of the gut mucosa and microbial translocation. These cells can secrete two isoforms of IL-17, IL-17A and IL-17F that are potent activators of neutrophilic inflammation at the gut mucosal tissue. In addition, Th17 cells produce IL-22 that plays a role in the maintenance of host defense and epithelial-barrier function. Studies report that Th17 cells are depleted during HIV/SIV infections and indicate that the depletion of these cells may accelerate the progression to AIDS. It is believed that HIV/SIV-specific Th17 cells may contribute to protection by enhancing the gut barrier function. None of the HIV vaccines developed so far have been shown to elicit IL-17 producing CD4 T cells. Data herein indicates that it is possible to do so using the recombinant *L. lactis*.

EXAMPLES

Addition of HIV Gag p24 on the Tip of the T3 Pilus in *L. lactis*

The backbone of the pilus in Gram-positive bacteria is composed of multiple covalently linked identical subunits (major pilin), to which one or more minor pilin subunits are covalently attached. Pilin proteins are synthesized with an N-terminal Sec signal, which is cleaved during transit through the cytoplasmic membrane, and a C-terminal cell wall sorting signal (CWSS), which contains an LPXTG (or similar) amino acid motif, followed by a hydrophobic region and a positively charged C terminus. Pilus assembly is catalyzed by a pilus-specific sortase family transpeptidase, which cleaves the CWSS motif between the threonine (T) and glycine (G) residues and forms a covalent bond between this T and a conserved lysine (K) residue of another major pilin subunit. As this process repeats, the pilus is polymerized until it is covalently linked to the cell wall by either the "housekeeping" sortase, which is responsible for anchoring most surface proteins of Gram-positive bacteria to the cell wall, or the pilus-specific sortase.

In *Streptococcus pyogenes*, the T3 pilus locus encodes the major pilin (T3) and the minor pilins Cpa and OrfB, the pilus-specific transpeptidase SrtC2, and SipA2, which is required for pilus polymerization by SrtC2. The lysine residue 173 (K173) and the CWSS (QVPTG) of the T3 major pilin subunit are required for polymerization of T3. This indicates that individual T3 subunits are polymerized into the pilus structure by covalent bonds between K173 of T3 and the threonine of the CWSS (T315) of the adjacent T3 subunit. K173 of T3, along with the CWSS (VPPTG) of Cpa, are required for incorporation of the minor pilin, Cpa, into the pilus. Thus, the K173 residue of T3 is required for T3-T3 linkage and is also required for covalent linkage of Cpa to the T3 pilus. Cpa is located at the tip of T3 pili.

The *L. lactis* does not express pili and thus an operon from GAS was used that encodes all proteins required for formation of pilus. See Quigley et al., Infect Immun. 2010, 78(3):1294-303. The genetic locus in which GAS pili are encoded has been named the FCT (fibronectin-binding, collagen binding, T antigen) region for the proteins it encodes. The FCT-3 locus encodes 4 proteins for the formation of the pilus (FIG. 1). The protein encoded by the first gene in the operon, cpa, is incorporated at the pilus tip. The second gene (sipA2) is essential for pilus polymerization. This gene is followed by tee3, which encodes the shaft protein, T3, and by srtC2, which encodes the pilin polymerase. A *L. lactis* strain containing cpa, sipA, srtC2 and tee3 was constructed and examined by immunodot blots of whole cells and by western blot of cell wall extracts heated in SDS to dissociate non-covalent bonds. These data indicate the presence of multimers of T3 pili. Furthermore, these pili could be visualized by immunogold electron microscopy.

HIV-1 clade B Gag p24 was used as a model protein to demonstrate that one can engineer a foreign protein covalently linked to the T3 pilus tip and that it would be expressed in *L. lactis* on pili. The gene for p24 was inserted between the coding sequences for the signal sequence at the N terminus of Cpa (contains the first 11 amino acids of the mature Cpa protein) and the CWSS at the C terminus of Cpa (contains the 119 amino acids from the C terminus of mature processed Cpa) in the plasmid that also encodes SipA2, SrtC2 and T3, and transformed the construct into *L. lactis*.

The Cpa_Gagp24_Nucleotide (1317nt) is
(SEQ ID NO: 1)
TTGCAAAAGAGGGATAAAACCAATTATGGAAGCGCTAACAACAAACGACG

ACAAACGACGATCGGATTACTGAAAGTATTTTTGACGTTTGTAGCTCTGA

TAGGAATAGTAGGGTTTTCTATCAGAGCGTTCGGAGCTGAAGAACAATCA

GTGCCAAATAAACAAAGCCCTATAGTGCAGAACATCCAGGGGCAAATGGT

ACATCAGGCCATATCACCTAGAACTTTAAATGCATGGGTAAAAGTAGTAG

AAGAGAAGGCTTTCAGCCCAGAAGTGATACCCATGTTTTCAGCATTATCA

GAAGGAGCCACCCCACAAGATTTAAACACCATGCTAAACACAGTGGGGGG

ACATCAAGCAGCCATGCAAATGTTAAAAGAGACCATCAATGAGGAAGCTG

CAGAATGGGATAGAGTGCATCCAGTGCATGCAGGGCCTATTGCACCAGGC

CAGATGAGAGAACCAAGGGGAAGTGACATAGCAGGAACTACTAGTACCCT

TCAGGAACAAATAGGATGGATGACAAATAATCCACCTATCCCAGTAGGAG

AAATTTATAAAAGATGGATAATCCTGGGATTAAATAAAATAGTAAGAATG

TATAGCCCTACCAGCATTCTGGACATAAGACAAGGACCAAAGGAACCCTT

TAGAGACTATGTAGACCGGTTCTATAAAACTCTAAGAGCCGAGCAAGCTT

CACAGGAGGTAAAAAATTGGATGACAGAAACCTTGTTGGTCCAAAATGCG

AACCCAGATTGTAAGACTATTTTAAAAGCATTGGGACCAGCGGCTACACT

AGAAGAAATGATGACAGCATGTCAGGGAGTAGGAGGACCCGGCCATAAGG

CAAGAGTTTTGAAGTTAACTATTTCTAAAACTGTTACTGGAACTATTGCA

GATAAGAAAAAGAATTTAACTTTGAAATACATTTAAAATCTTCTGATGG

ACAAGCTATAAGTGGAACATATCCGACAAACTCTGGAGAACTCACAGTTA

CAGATGGAAAAGCTACCTTCACATTAAAGGATGGAGAATCATTGATTGTT

GAGGGGCTACCTTCAGGTTACTCTTATGAAATTACAGAAACGGGTGCTTC

AGATTATGAGGTAAGTGTTAATGGAAAAAATGCACCAGATGGAAAAGCGA

CGAAAGCCTCAGTTAAGGAAGATGAGACTGTAGCTTTTGAAAACCGAAAA

GATCTTGTCCCACCAACTGGTTTGACAACAGATGGGGCTATCTATCTTTG

GTTGTTATTACTTGTTCCATTTGGGTTATTGGTTTGGCTATTTGGTCGTA

AAGGGACTAAAAAATGA.

The Cpa_Gagp24_Protein (438) is
(SEQ ID NO: 2)
LQKRDKTNYGSANNKRRQTTIGLLKVFLTFVALIGIVGFSIRAFGAEEQS

VPNKQSPIVQNIQGQMVHQAISPRTLNAWVKVVEEKAFSPEVIPMFSALS

EGATPQDLNTMLNTVGGHQAAMQMLKETINEEAAEWDRVHPVHAGPIAPG

QMREPRGSDIAGTTSTLQEQIGWMTNNPPIPVGEIYKRWIILGLNKIVRM

YSPTSILDIRQGPKEPFRDYVDRFYKTLRAEQASQEVKNWMTETLLVQNA

NPDCKTILKALGPAATLEEMMTACQGVGGPGHKARVLKLTISKTVTGTIA

DKKKEFNFEIHLKSSDGQAISGTYPTNSGELTVTDGKATFTLKDGESLIV

EGLPSGYSYEITETGASDYEVSVNGKNAPDGKATKASVKEDETVAFENRK

DLVPPTGLTTDGAIYLWLLLLVPFGLLVWLFGRKGTKK.

Figure 2:
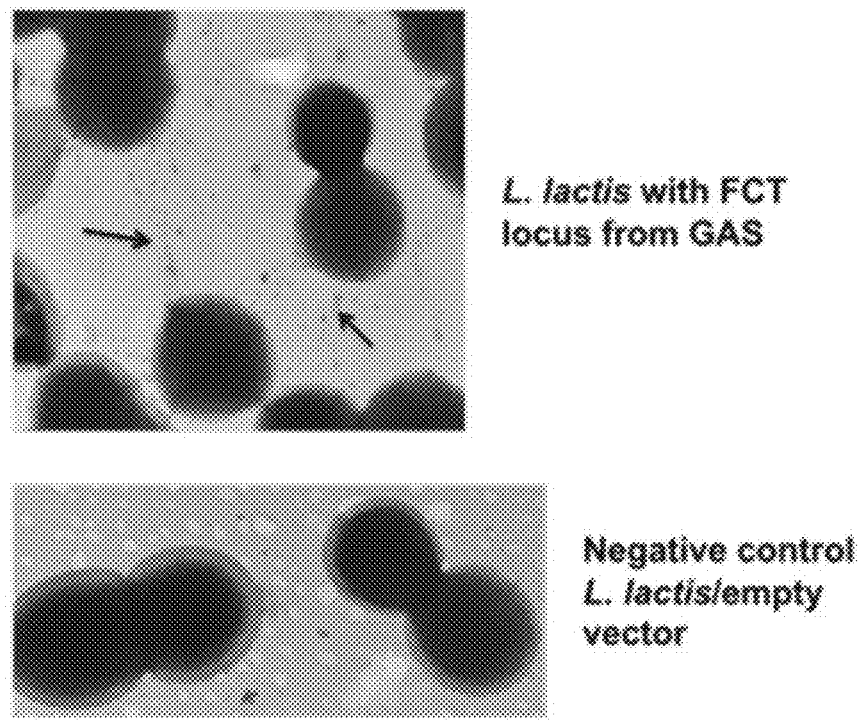
FIG. 2 shows data on the detection of T3 pili on the surface of *L. lactis* containing FCT locus from group A *Lactococcus* (cpa, sipA, srtC2 and tee3) by immunogold using anti-T3 Antibody. Arrows point to pili.
Figure 3:
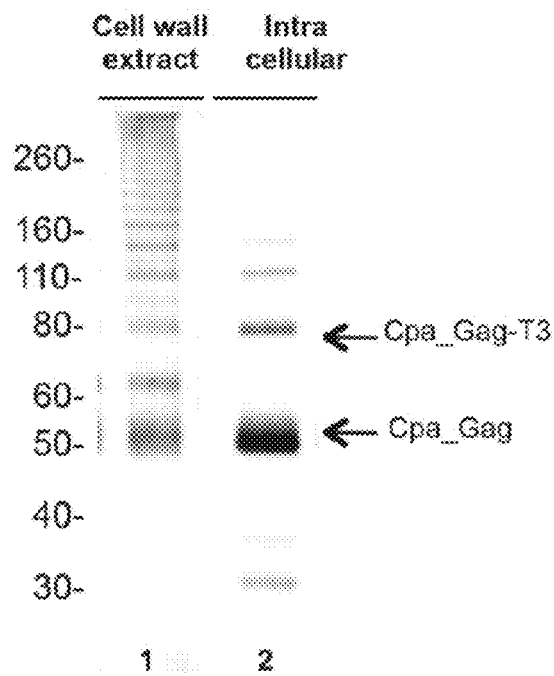
FIG. 3 shows western blot analysis of recombinant *L. lactis* cell wall extract and intracellular fraction using an anti-Gag antibody following treatment with hot SDS.

This plasmid was generated by replacing the MBP in pJRS9565 described in Quigley et al., Infect Immun. 2010, 78(3):1294-303. The protein expression is driven by the P23 promoter. The resulting strain expresses p24 on its surface based on dot blot analysis. Western blots of cell wall extracts of these strains demonstrated that p24 is covalently attached to the T3 pilus in *L. lactis*, since it is present in the high molecular weight fraction following treatment with hot SDS (FIG. 2). Because there is only one molecule of p24 but many of T3 on each pilus, reactivity with anti-p24 is stronger for the lower molecular weight pili, while reactivity with anti-T3 is stronger for higher molecular weight forms.

Figure 4A:
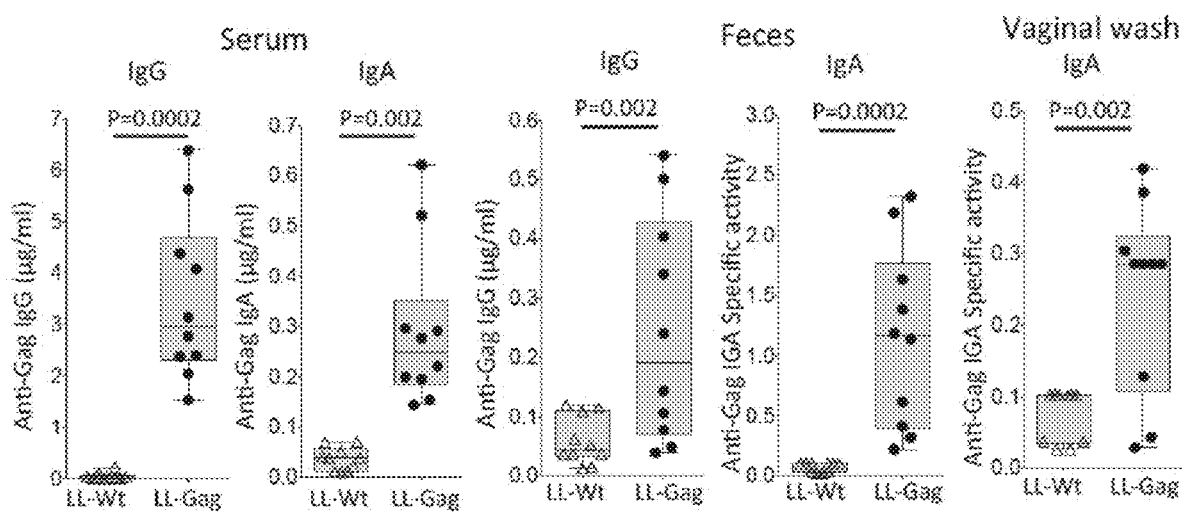
FIG. 4A shows experimental data. Anti-Gag IgG and IgA levels in the serum, feces, and vaginal wash of mice immunized with either wild-type *L. lactis* (LLWt) or *L. lactis* expressing HIV Gag p24 (LLGag). Mice were immunized intragastrically (IG) on weeks 0, 4, 8 and 12 with each immunization consisting of three daily doses of either LL-Wt or LL-Gag ($5 \times 10^9$ cfu/dose). Data is representative of two weeks after the fourth immunization. IgG levels in the vaginal wash were at the level of background.

Oral Administration of *L. lactis* Expressing Gag p24 on the Cell Wall Induces a Strong Mucosal and Systemic Humoral Immunity in Mice Mice were immunized by orally administering the *L. lactis* expressing HIV Gag p24 on weeks 0, 4, 8 and 12. Each immunization consisted of three daily doses with $5 \times 10^9$ cfu/dose in a volume of 50 µl. Serum, feces and vaginal secretions were collected on day 14 following the fourth immunization and analyzed for Gag-specific IgG and IgA in serum, feces and vaginal wash. These experiments revealed Gag-specific IgA responses in serum, feces and vaginal wash (FIG. 4A). Gag-specific IgG responses were also observed in serum and feces (FIG. 4A).

Figure 4B:
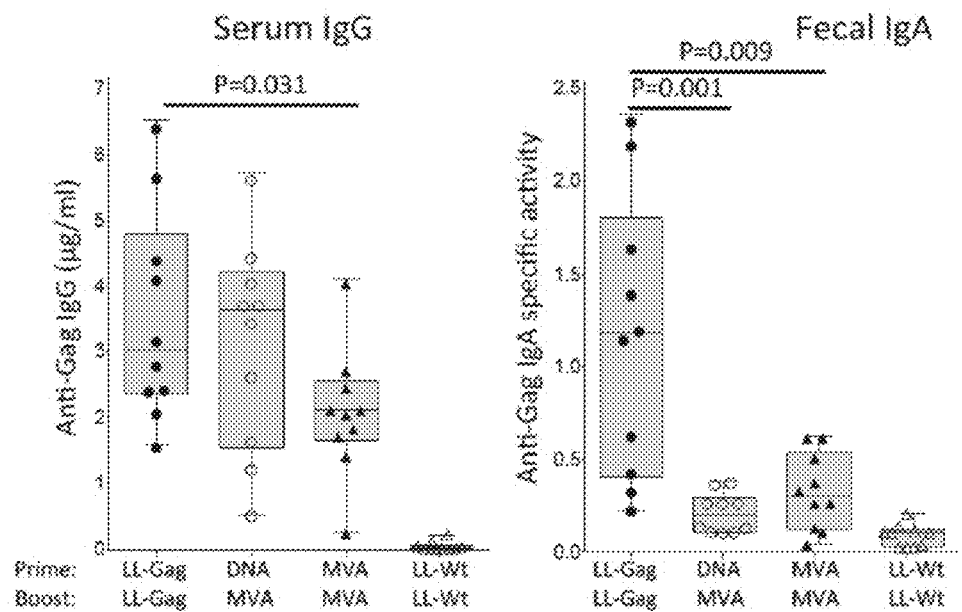
FIG. 4B shows data. Gag-specific serum IgG and mucosal IgA in mice immunized with differing vaccine modalities. Mice were immunized in a prime-boost model. LL immunizations were delivered orally. DNA and MVA immunogens expresses HIV Gag and were delivered intramuscularly at a dose of 50 ug and $1 \times 10^8$ pfu, respectively. The priming immunization for these two groups was at week 0 and the boost was at week 4. Analyses were done at 2 weeks after the final immunization.

To further confirm the benefit of oral *L. lactis* immunizations to elicit strong mucosal antibody responses over intramuscular vaccines, serum and mucosal responses were compared between oral *L. lactis* and intramuscular DNA prime/MVA boost vaccine or MVA prime/MVA boost vaccine. Impressively, the Gag-specific IgA responses in feces were significantly higher in the *L. lactis* group than in the DNA/MVA or MVA/MVA groups (FIG. 4B). Moreover, a similar effect on IgG responses was observed in serum. These results demonstrate that oral immunization with *L. lactis* induces a strong mucosal and systemic IgA and IgG responses in mice.

Figure 5A:
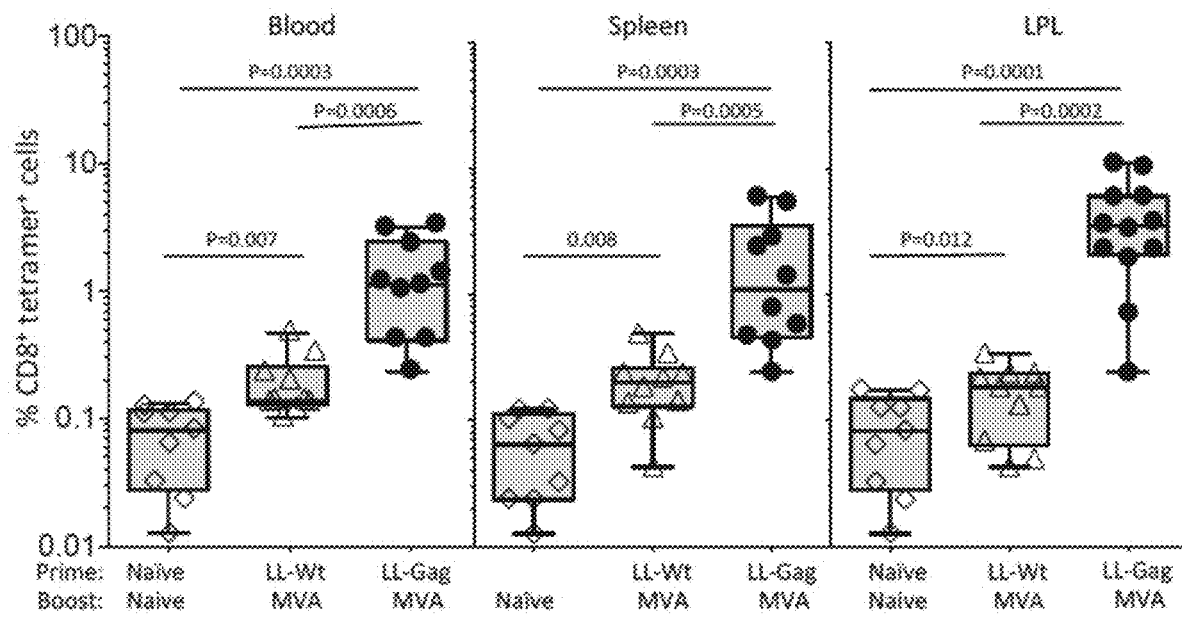
FIG. 5A shows experimental data. Gag-specific $CD8^+$ responses in the blood, spleen, and lamina propria lymphocytes (LPL) one-week post MVA (IM) boost. Mice were primed with LL-Wt (IG) or LL-Gag (IG). Naïve animals received neither *L. lactis* nor MVA.
Figure 5B:
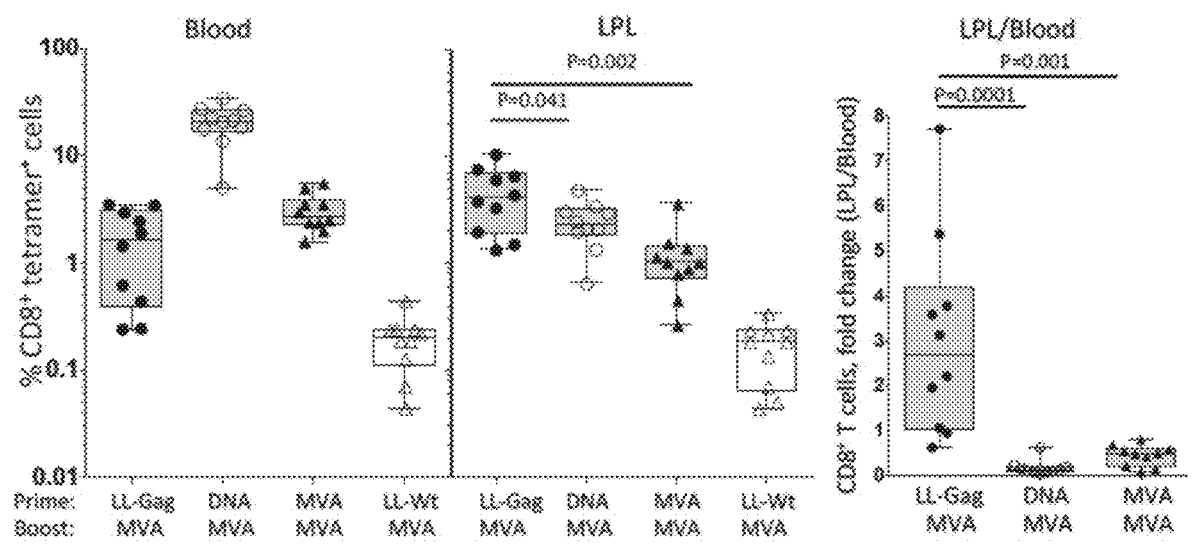
FIG. 5B shows data. Gag-specific $CD8^+$ responses in the blood and LPL of mice one-week post MVA (IM) boost. Mice were primed with LL-Gag (IG), DNA (IM), MVA (IM), or LL-Wt (IG). The ratio of $CD8^+$ responses in the LPL vs. the blood shows a preferential induction of Gag-Specific $CD8^+$ T-cells at the mucosal surfaces when priming with LL-Gag. Immunizations are as described under FIG. 4B.

Oral *L. lactis* Prime Combined with Intramuscular MVA Boost Elicits a Strong Mucosal and Systemic Cellular Immunity in Mice In the above experiment, detectable levels of Gag specific CD8 T cell responses were not observed following *L. lactis* immunizations in the blood. However, when these *L. lactis* primed mice were boosted with MVA expressing Gag intramuscularly, Gag-tetramer-specific CD8 T cell responses were observed in blood, spleen and small intestine laminapropria lymphocytes (LPLs) at 1 week following the MVA boost (FIG. 5A). The CD8 T cell response was thought to be due to priming by *L. lactis* immunization, as significant responses in mice for prime and boosted that received wt-*L. lactis* with MVA/Gag was not observed. As with the antibody responses, to further confirm the benefit of oral *L. lactis* immunizations to elicit strong mucosal CD8 T cell responses over intramuscular vaccines, blood and gut responses were compared between oral *L. lactis*/MVA regimen and intramuscular DNA/MVA or MVA/MVA regimens (FIG. 5B). Impressively, the Gag-specific CD8 T cell responses in the gut were significantly higher in the *L. lactis*/MVA group than in the DNA/MVA or MVA/MVA groups (FIG. 5B). In addition, the ratio of Gag-specific CD8 T cells between LPLs and blood was also significantly higher in the *L. lactis*/MVA group than in the DNA/MVA or MVA/MVA groups (FIG. 5B). These results demonstrate that oral priming with *L. lactis* and intramuscular boosting with MVA induces very high levels of Gag-specific CD8 T cells in the gut and blood.

Figure 6:
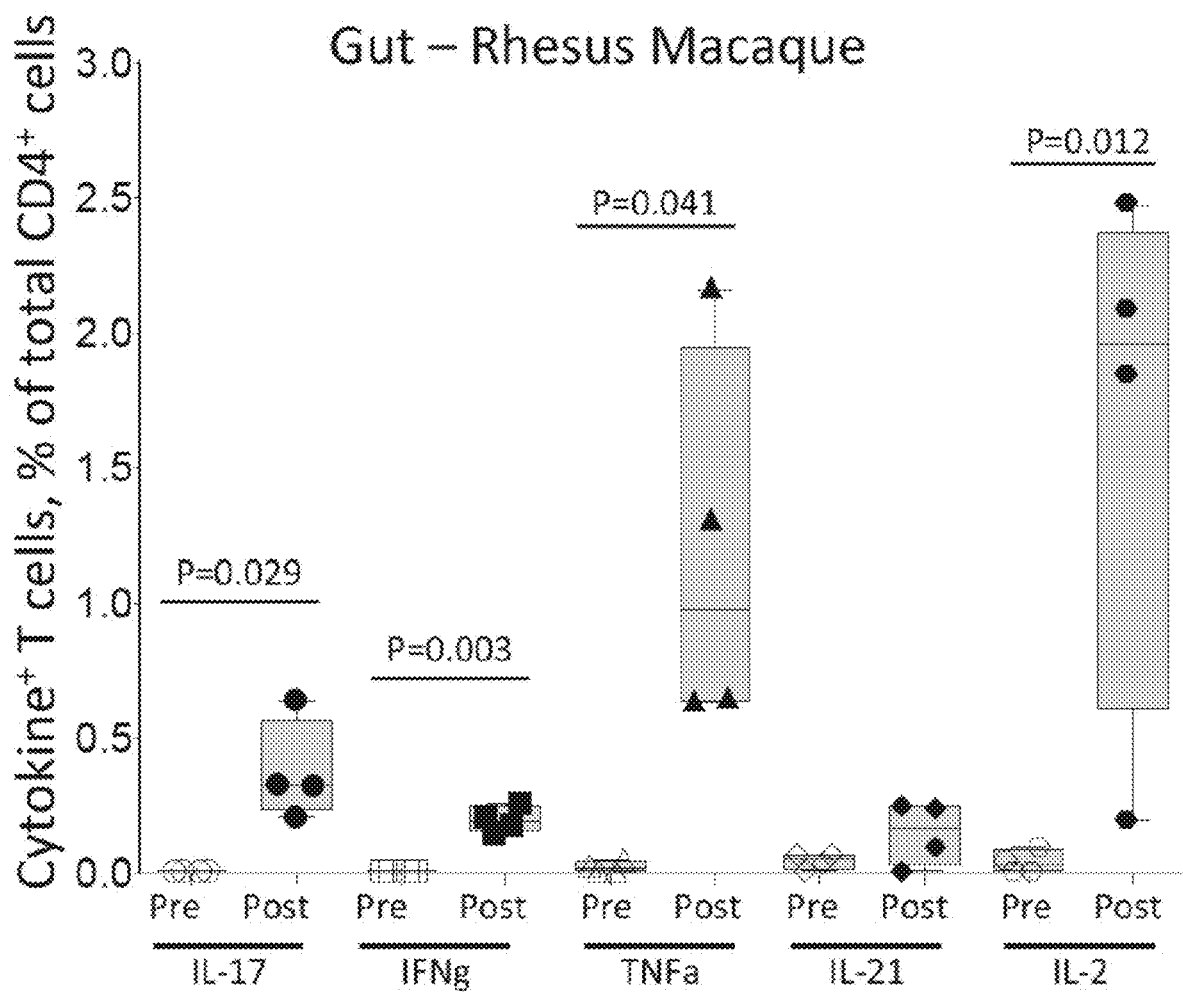
FIG. 6 shows data on cytokine expression of gut CD4+ T-cells pre and post stimulation with Gag peptides in rhesus macaques immunized with LL-Gag (IG) two weeks after the fourth immunization.

Oral Administration of *L. lactis* Expressing Gag p24 Induces a Strong Gag-Specific CD4 T Cell Response with Unique Cytokine Expression Pattern (IL-2$^+$ IL-17$^+$) in the Rectum of Rhesus Macaques In a pilot study, four rhesus macaques were immunized by orally administering the *L. lactis* expressing HIV Gag p24 on weeks 0, 4, 8 and 12. See FIG. 6. Each immunization consisted of three daily doses with $5 \times 10^{10}$ cfu/dose in a volume of 1 ml. Gag-specific CD4 and CD8 T cell responses were measured in the rectum and blood at 2 weeks after each vaccination. Impressively, strong Gag-specific CD4 T cells were observed in the rectum. The CD4 responses in the blood were 10 times lower than in the rectum.

Interestingly, the Gag-specific CD4 T cells in the rectum had a unique cytokine expression pattern such that they predominantly produced IL-2, followed by TNFα followed by IL-17 and very little IFNγ. For example, SIV-specific CD4 T cells in SIV infected animals predominantly produce IFNγ and TNFα with little IL-2 and no IL-17. It is important to note that IL-2 is a key cytokine for T cell proliferation and survival, and IL-17 plays a role in maintaining the barrier function of gut epithelium. It has not previously been possible to generate HIV/SIVCD4 T cells that produce IL-17 by vaccination, and these experiments indicate that it is possible to do so with oral immunization with *L. lactis*. It is contemplated that these CD4 T cells influence the antibody response and protection from mucosal SIV challenge. As seen in mice, oral *L. lactis* immunizations alone did not elicit detectable levels of Gag-specific CD8 T cells; however the process of boosting these animals with MVA expressing HIV Gag is thought to improve the mucosal antibody response.

Figure 7:
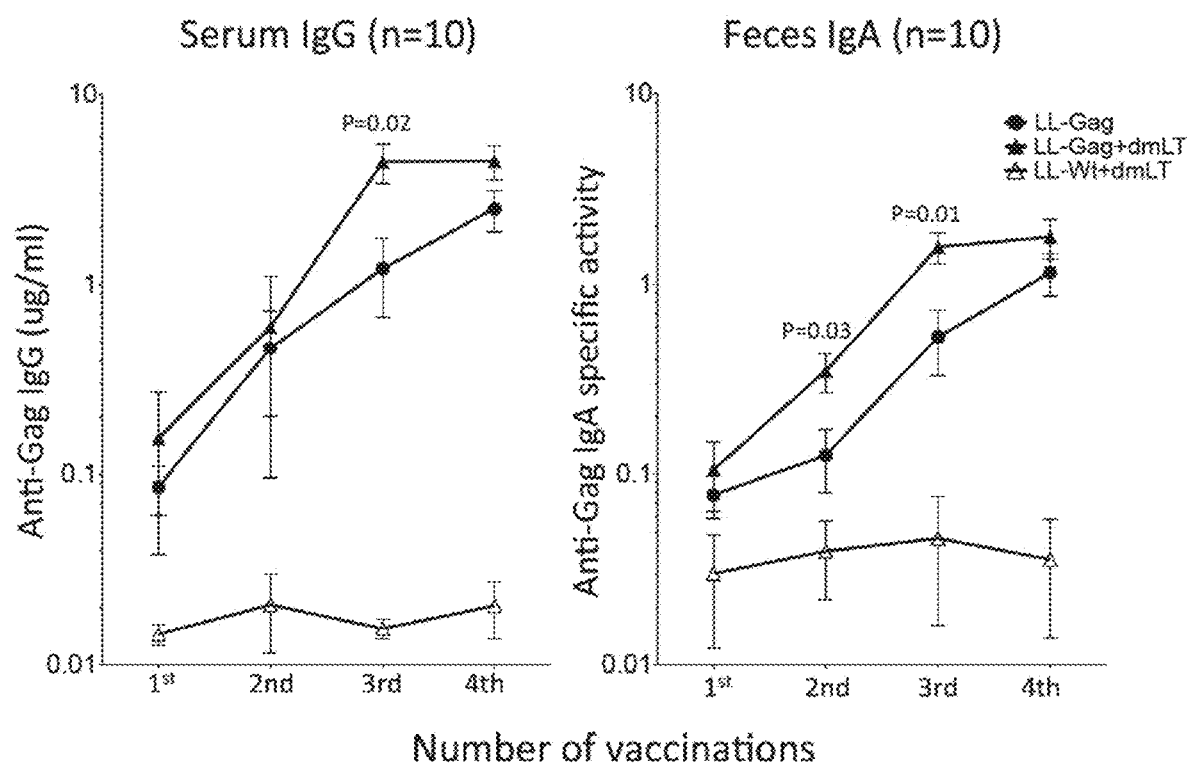
FIG. 7 shows data of the adjuvant activity of dmLT in mice. Mice were vaccinated orally with *L. lactis* expressing Gag 24p on the tip of the pilus in the absence and presence of dmLT. Analyses were done 2 weeks after each immunization.

The Adjuvant dmLT Enhances the IgG and IgA Responses Elicited by *L. lactis* in the Serum and Feces in Mice Examples of potential of three adjuvants to be used in combinations with the *L. Lactis* alone or with the prime boost method include double mutant *E. coli* heat-labile toxin (dmLT), Flagellin (TLR5 ligand), and CpG (TLR9 ligand). All three adjuvants can be delivered orally as soluble proteins/molecules. In mice, the dmLT induces strong IgA responses and moderate levels of Th responses, CpG induces strong CD8 T cell responses and flagellin induces moderate levels of both IgA and T cell responses. Experiments demonstrate that dmLT enhances the IgG and IgA responses elicited by *L. lactis* in the serum and feces in mice (FIG. 7).

What we claim:

1. A composition comprising a gram-positive bacterium comprising a recombinant nucleic acid encoding a polypeptide chimera having an HIV antigen and encoding heterologous proteins capable of forming pili on the bacterium, wherein bacterium expresses the HIV antigen on the tip of the pili, and wherein the polypeptide chimera comprises an amino acid sequence of SEQ ID NO: 2.

2. The composition of claim 1, wherein the bacterium is *L. lactis*.

3. The composition of claim 1, wherein the recombinant nucleic acid encoding HIV antigen is configured between N terminus amino acids of a Cpa protein of a group A *Streptococcus* and C terminus amino acids from the Cpa.

4. The composition of claim 3 wherein the HIV antigen is Gag p24.

* * * * *